United States Patent
Lin et al.

(10) Patent No.: US 8,632,893 B2
(45) Date of Patent: *Jan. 21, 2014

(54) ORGANIC COMPOUND AND ORGANIC ELECTROLUMINESCENCE DEVICE EMPLOYING THE SAME

(75) Inventors: Chi-Jen Lin, Yingge Township (TW); Heh-Lung Huang, Yingge Township (TW); Jin-Sheng Lin, Tainan (TW); Chien-Hong Cheng, Hsinchu (TW); Mei-Rurng Tseng, Hsinchu (TW)

(73) Assignee: Industrial Technology Research Institute (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/233,456

(22) Filed: Sep. 15, 2011

(65) Prior Publication Data

US 2012/0001537 A1 Jan. 5, 2012

Related U.S. Application Data

(63) Continuation-in-part of application No. 12/340,145, filed on Dec. 19, 2008, now Pat. No. 8,173,274.

(30) Foreign Application Priority Data

Jul. 22, 2008 (TW) .............................. 97127784 A

(51) Int. Cl.
*H01L 51/54* (2006.01)
*C07D 219/00* (2006.01)

(52) U.S. Cl.
USPC ........... 428/690; 313/504; 313/506; 546/102; 546/107; 428/917

(58) Field of Classification Search
None
See application file for complete search history.

(56) References Cited

U.S. PATENT DOCUMENTS

| | | | |
|---|---|---|---|
| 7,014,925 B2 | 3/2006 | Thoms | |
| 7,056,601 B2 | 6/2006 | Cosimbescu et al. | |
| 7,227,027 B2 | 6/2007 | Qiu et al. | |
| 7,252,893 B2 | 8/2007 | Ricks et al. | |
| 8,173,274 B2 * | 5/2012 | Lin et al. ........................ | 428/690 |
| 2003/0205696 A1 | 11/2003 | Thoms et al. | |
| 2004/0209115 A1 | 10/2004 | Thompson et al. | |
| 2004/0209116 A1 | 10/2004 | Ren et al. | |
| 2004/0219386 A1 | 11/2004 | Thoms | |
| 2004/0247933 A1 | 12/2004 | Thoms | |
| 2006/0088728 A1 | 1/2006 | Chung et al. | |
| 2007/0141391 A1 | 6/2007 | Coggan et al. | |
| 2007/0173657 A1 | 7/2007 | Chen et al. | |

FOREIGN PATENT DOCUMENTS

| | | |
|---|---|---|
| WO | WO 2007/110228 | 10/2004 |
| WO | WO 2006/033563 | 3/2006 |
| WO | WO 2006/033564 | 3/2006 |
| WO | WO 2006/080637 | 3/2006 |

OTHER PUBLICATIONS

Kosolapoff et al., Journal of American Chemical Society, vol. 76, (1954), pp. 1276-1278.
Vak et al., Macromolecules, (2006), vol. 39, pp. 6433-6439.
Machine translation of description section for WO2007/110228 A1, which was published Oct. 2007.
Notice of Allowance dated Apr. 3, 2012 from corresponding application No. TW 97127784.

* cited by examiner

*Primary Examiner* — Dawn L. Garrett
(74) *Attorney, Agent, or Firm* — Lowe Hauptman & Ham, LLP

(57) ABSTRACT

Organic compounds and organic electroluminescence devices employing the same are provided. The organic compound has a chemical structure represented as follows:

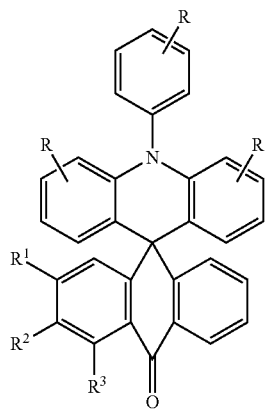

wherein R are each independently an hydrogen, or a $C_{1-8}$ alkyl group, and wherein $R^1$ and $R^2$ are each independently an hydrogen, or a $C_{1-8}$ alkyl group, $R^3$ is a hydrogen, and $R^1$ and $R^2$ are not hydrogen group simultaneously; or wherein $R^1$ and $R^2$ link together with the carbon atoms bonded thereto to form a phenyl group;

wherein $R^2$ and $R^3$ link together with the carbon atoms bonded thereto to form a phenyl group.

6 Claims, 1 Drawing Sheet

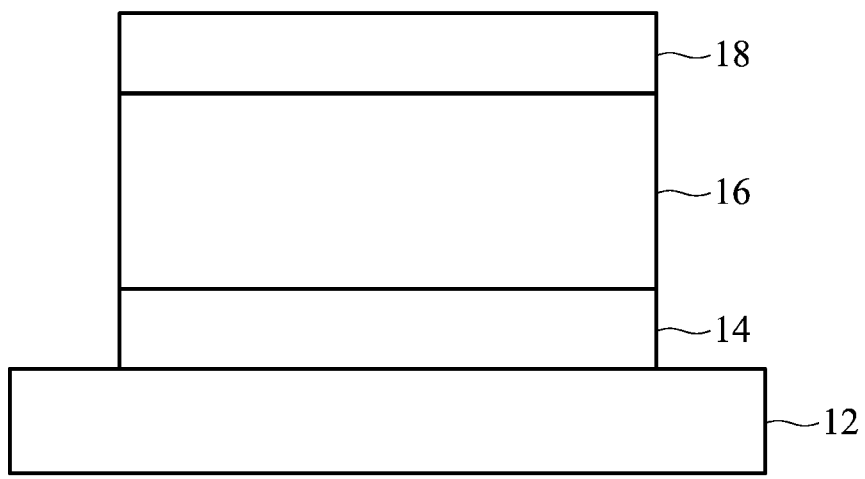

ORGANIC COMPOUND AND ORGANIC ELECTROLUMINESCENCE DEVICE EMPLOYING THE SAME

CROSS REFERENCE TO RELATED APPLICATIONS

This application is a Continuation-In-Part of pending U.S. patent application Ser. No. 12/340,145, filed Dec. 19, 2008 and entitled "Organic compound and Organic electroluminescence device employing the same", which claims priority of Taiwan Patent Application No. 97127784, filed on Jul. 22, 2008.

BACKGROUND OF THE INVENTION

1. Field of the Invention

The invention relates to an organic compound and organic electroluminescence device employing the same and, more particularly, to an organic compound serving as host material and a phosphorescent organic electroluminescence device employing the same.

2. Description of the Related Art

Recently, with the development and wide application of electronic products, such as mobile phones, PDAs, and notebook computers, there has been increasing demand for flat display elements which consume less electric power and occupy less space. Organic electroluminescent devices are self-emitting and highly luminous, with wider viewing angles, faster response speeds, and simpler fabrication methods, making them an industry display of choice.

Generally, an organic electroluminescent device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission.

Depending on the spin states of the hole and electron, the exciton which results from the hole and electron recombination can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of the OLED.

In application of organic electroluminescent devices, phosphorescent guest materials have to be used in combination with host materials which has an energy gap matched therewith, thereby achieving optimal electroluminescent performance and quantum yield. Particularly, since blue and green host materials require larger differences of energy gap between the host and guest material for electroluminescence, the host materials used in phosphorescent OLED should have a shorter conjugated system. Further, in order to keep the key characteristic of the organic compound used in OLED (i.e. thermal-stability), the host material should also have larger molecular weight, resulting in difficulties for chemical structure designs.

Certain organic compounds have been disclosed, using green or blue phosphorescent OLEDs, such as US Patent 2003/0205696A1 and US Patent 2007/0141391A1. Most of the disclosed organic compounds have the moieties of carbazole or silyl benzene derivatives. However, the aforementioned compounds exhibit inferior thermal-stability or results in low current density of the OLED device.

Therefore, it is necessary to develop novel organic compounds suitable for phosphorescent OLEDs to solve the above problems.

BRIEF SUMMARY OF THE INVENTION

An exemplary embodiment of an organic compound has a Formula (I), of:

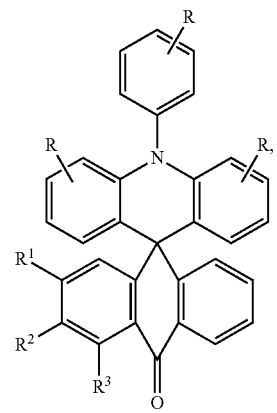

wherein R are each independently an hydrogen, or a $C_{1-8}$ alkyl group, and wherein $R^1$ and $R^2$ are each independently an hydrogen, or a $C_{1-8}$ alkyl group, $R^3$ is a hydrogen, and $R^1$ and $R^2$ are not hydrogen group simultaneously; or wherein $R^1$ and $R^2$ link together with the carbon atoms bonded thereto to form a phenyl group; or wherein $R^2$ and $R^3$ link together with the carbon atoms bonded thereto to form a phenyl group.

In another exemplary embodiment of the invention, an organic electroluminescence device is provided. The device includes a pair of electrodes; and an electroluminescent element disposed between the pair of electrodes, wherein the electroluminescent element includes the aforementioned organic compound.

Yet another exemplary embodiment of the invention provides an organic electroluminescence device including an emission layer which includes a host material and a phosphorescent dopant. Particularly, the host material includes the aforementioned organic compound and the emission layer emits blue or green light under a bias voltage.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein:

FIG. 1 shows a cross section of an organic electroluminescent device disclosed by an embodiment of the invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Organic Compound

The invention provides triarylaminec compounds with a spiro structure and an organic electroluminescence device including the same, wherein the triarylaminec compounds has a Formula (I), of:

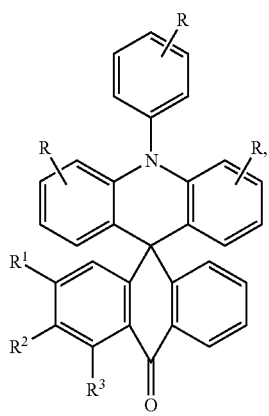

wherein R are each independently an hydrogen, or a $C_{1-8}$ alkyl group, and wherein $R^1$ and $R^2$ are each independently an hydrogen, or a $C_{1-8}$ alkyl group, $R^3$ is a hydrogen, and $R^1$ and $R^2$ are not hydrogen group simultaneously; or wherein $R^1$ and $R^2$ link together with the carbon atoms bonded thereto to form a phenyl group; or wherein $R^2$ and $R^3$ link together with the carbon atoms bonded thereto to form a phenyl group.

According to an embodiment of the disclosure, $R^1$, and $R^2$ are each independently a methyl group, ethyl group, propyl group, isopropyl group, butyl group, tert-butyl group, methoxy group, ethoxy group, propoxy group, isopropoxy group, butoxy group, or an isobutoxy group.

The organic compounds according to Formula (I) of the invention include the following compounds shown in Table 1. In addition, the contraction thereof are also named and shown in Table 1.

TABLE 1

| Example | structure | contraction |
|---|---|---|
| 1 |  | TB |
| 2 | 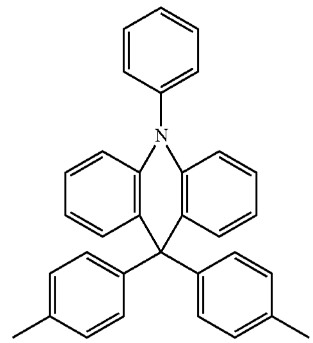 | TMB |
| 3 | 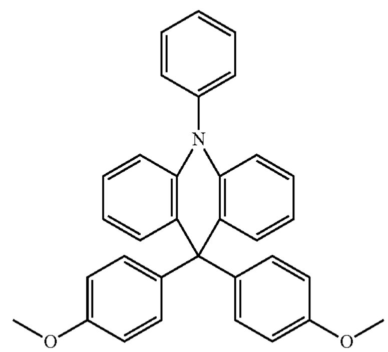 | TBM |
| 4 | 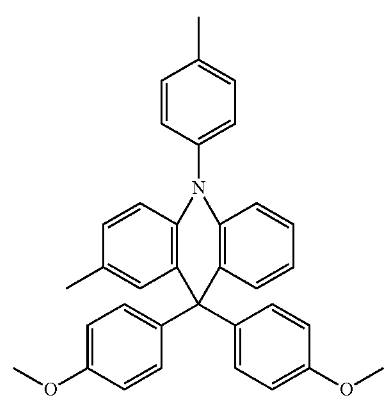 | MTBM |
| 5 | 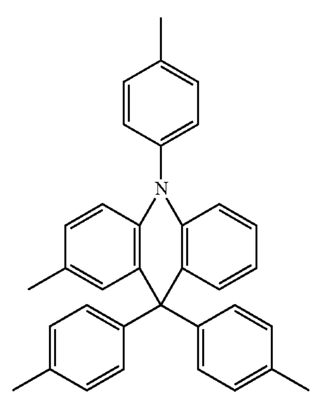 | MTMB |

TABLE 1-continued

| Example | structure | contraction |
|---------|-----------|-------------|
| 6 | 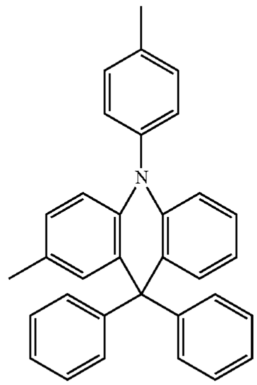 [SMILES: Cc1ccc(N2c3ccccc3C(c3ccccc3)(c3ccccc3)c3cc(C)ccc32)cc1] | MTB |
| 7 | 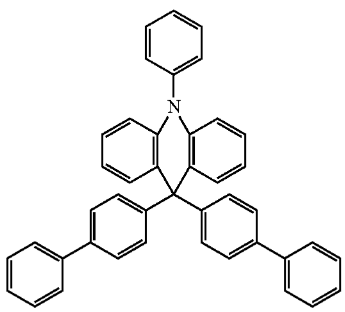 [SMILES: c1ccc(-c2ccc(C3(c4ccc(-c5ccccc5)cc4)c4ccccc4N(c4ccccc4)c4ccccc43)cc2)cc1] | TBP |
| 8 | 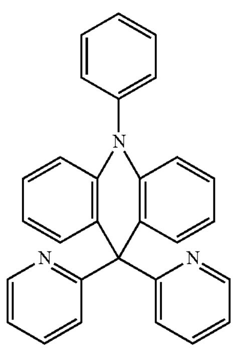 [SMILES: c1ccc(N2c3ccccc3C(c3ccccn3)(c3ccccn3)c3ccccc32)cc1] | TP |
| 9 | 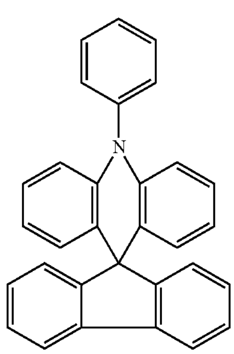 [SMILES: c1ccc(N2c3ccccc3C3(c4ccccc4-c4ccccc43)c3ccccc32)cc1] | TF |
| 10 | | MTF |
| 11 | | DAT |
| 12 | | MDAT |
| 13 | | DTAT |

TABLE 1-continued

| Example | structure | contraction |
|---|---|---|
| 14 | 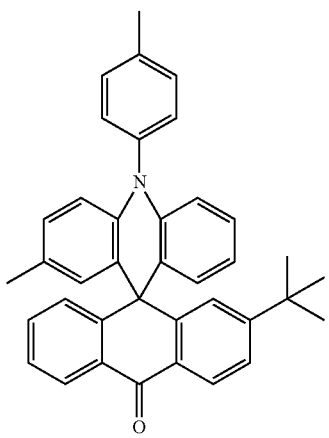 [SMILES: Cc1ccc(N2c3ccccc3C3(c4ccccc4C(=O)c4ccc(C(C)(C)C)cc43)c3cc(C)ccc32)cc1] | MDTAT |
| 15 | 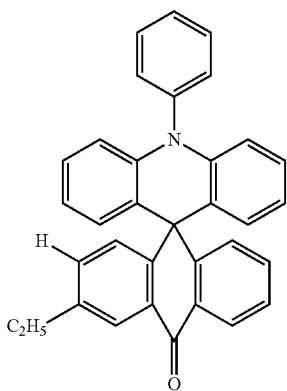 [SMILES: CCc1ccc2c(c1)C(=O)c1ccccc1C21c2ccccc2N(c2ccccc2)c2ccccc21] | DEAT |
| 16 | 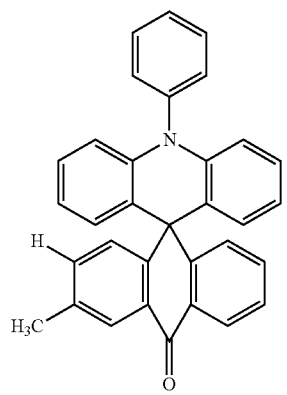 [SMILES: Cc1ccc2c(c1)C(=O)c1ccccc1C21c2ccccc2N(c2ccccc2)c2ccccc21] | DMAT |
| 17 | 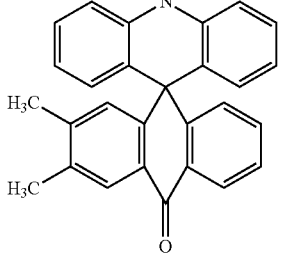 | DDMAT |
| 18 | 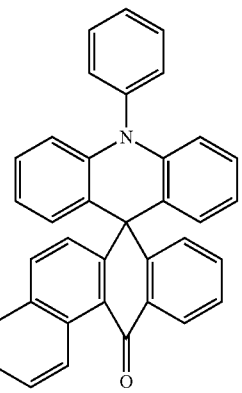 | DSBAT |
| 19 | 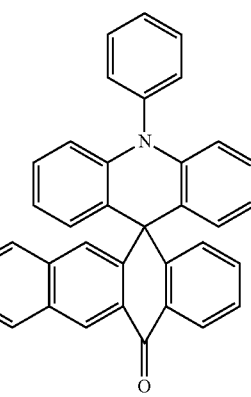 | DBAT |

In order to clearly illustrate the method for preparing organic compounds according to Formula (I), the preparation of compounds disclosed in Examples 1, 3, 7, 9, 11, 13 and 15-19 are described in detail as below.

EXAMPLE 1

Preparation of Compound TB

First, diphenylamine (10.0 mmole, 1.69 g), 1-bromo-2-iodobenzene (10.0 mmole, 2.82 g), and NaOtBu (25.0 mmole, 2.40 g) were add into a 100 ml bottle and dissolved into toluene (30 ml). Next, Pd(OAc)$_2$ (0.5 mmole, 0.11 g, 0.5 ml (1M in toluene)) was injected into the bottle and refluxed. After heating for 24 hrs, the reaction was terminated after being checked by a TLC, and the results were filtrated by a silica gel and a diatomite with Cl$_2$CH$_2$ as the extraction solvent After purification by column chromatography with n-hexane/ethyl acetate (9:1) as the extraction solvent, a compound A was obtained with a yield of 70%.

The synthesis pathway was as follows:

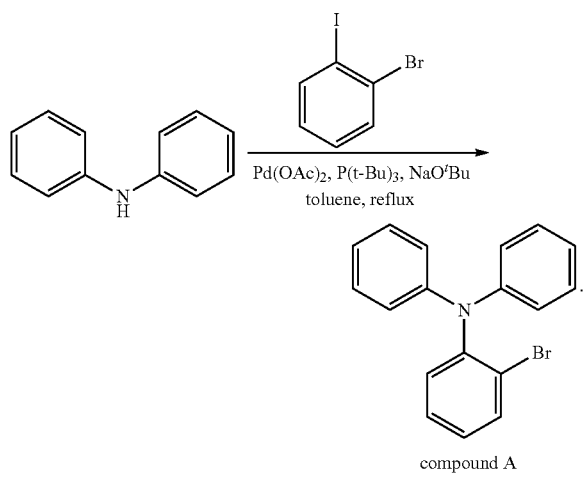

compound A

Next, a compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr, benzophenone (10.0 mmole, 1.82 g) was added into the bottle. After reacting at room temperature for 2 hrs, AcOH(30 ml) and HCl (3 ml) were added into the bottle and refluxed for 3 hrs. Next, the results was extracted by Cl$_2$CH$_2$ and dried by MgSO$_4$. After concentration, a compound TB (white powder) was obtained with a yield of 50%.

The synthesis pathway was as follows:

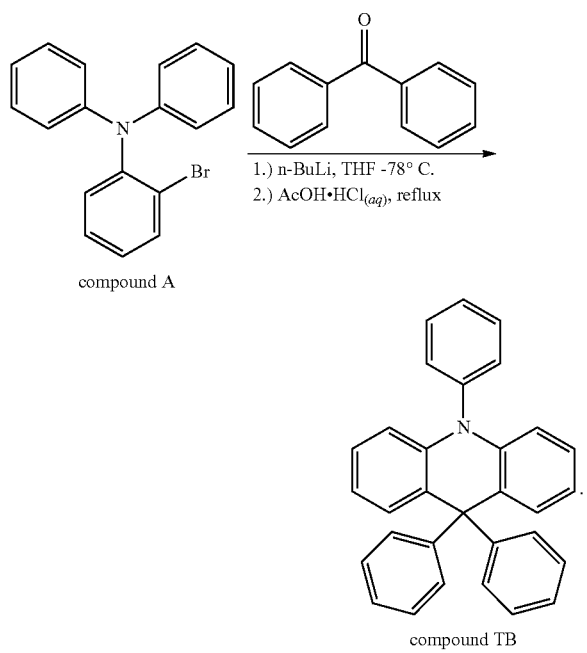

compound TB

Next, the TG, HOMO and LUMO energy gap, melting point, phosphorescent wavelength (measured at −78° C.), and $^1$Eg of compound TB were measured and are shown in Table 2.

EXAMPLE 3

Preparation of Compound TBM

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr, 4,4'-Dimethoxy benzophenone (10.0 mmole, 2.42 g) was added into the bottle. After reacting at room temperature for 2 hrs, AcOH (30 ml) and HCl (3 ml) were added into the bottle and refluxed for 3 hrs. Next, the results was extracted by Cl$_2$CH$_2$ and dried by MgSO$_4$, and gray powder was obtained via concentration. After reprecipitation with Cl$_2$CH$_2$ and n-hexane, a compound TBM (white powder) was obtained.

The synthesis pathway was as follows:

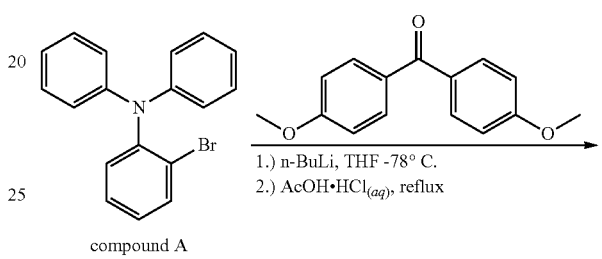

compound A

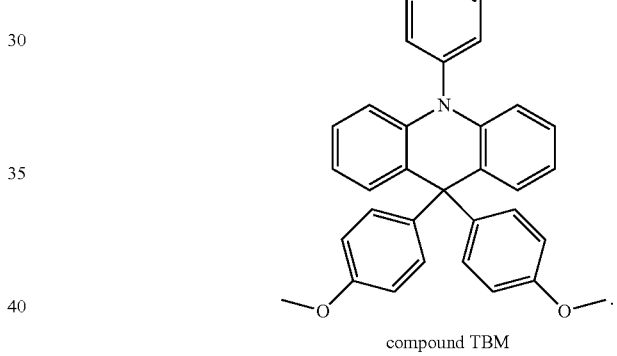

compound TBM

Next, the TG, HOMO and LUMO energy gap, melting point, phosphorescent wavelength (measured at −78° C.), and $^1$Eg of compound TBM were measured and are shown in Table 2.

EXAMPLE 7

Preparation of Compound TBP

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr, 4,4'-diphenyl benzophenone (10.0 mmole, 3.34 g) was added into the bottle. After reacting at room temperature for 2 hrs, AcOH (30 ml) and HCl (3 ml) were added into the bottle and refluxed for 3 hrs. Next, the results were extracted by Cl$_2$CH$_2$ and dried by MgSO$_4$, and gray powder was obtained via concentration. After reprecipitation with Cl$_2$CH$_2$ and n-hexane, a compound TBP (white powder) was obtained.

The synthesis pathway was as follows:

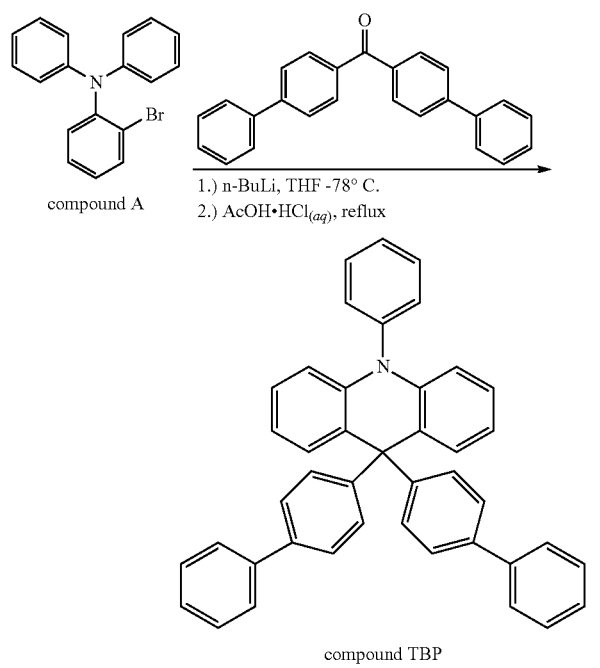

compound TBP

Next, the TG, HOMO and LUMO energy gap, melting point, phosphorescent wavelength (measured at −78° C.), and $^1$Eg of compound TBP were measured and are shown in Table 2.

EXAMPLE 9

Preparation of Compound TF

Compound A (10.0 mmole, 3.24 g) and THF (20 ml) were added into a bottle. After cooling to −78° C. n-BuLi (12.0 mmole, 0.77 g, 7.5 ml (1.6M in hexane)) was slowly added into the bottle. After stirring for 1 hr, fluorenone (10.0 mmole, 1.80 g) was added into the bottle. After reacting at room temperature for 2 hrs, AcOH (30 ml) and HCl (3 ml) were added into the bottle and refluxed for 3 hrs. Next, the results was extracted by Cl$_2$CH$_2$ and dried by MgSO$_4$, and gray powder was obtained via concentration. After reprecipitation with Cl$_2$CH$_2$ and n-hexane, a compound TF (white powder) was obtained with a yield of 64%.

The synthesis pathway was as follows:

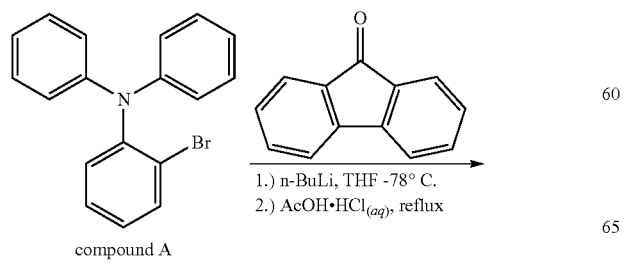

compound A

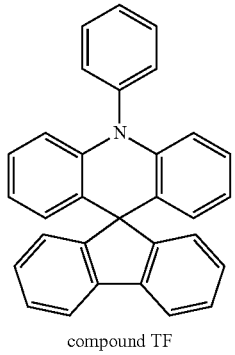

compound TF

Next, the TG, HOMO and LUMO energy gap, melting point, phosphorescent wavelength (measured at −78° C.), and $^1$Eg of compound TF were measured and are shown in Table 2.

EXAMPLE 11

Preparation of Compound DAT

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr, anthraquinone (10.0 mmole, 2.08 g) was added into the bottle. After reacting at room temperature for 2 hrs, AcOH (30 ml) and HCl (3 ml) were added into the bottle and refluxed for 3 hrs. Next, the results was extracted by Cl$_2$CH$_2$ and dried by MgSO$_4$, and gray powder was obtained via concentration. After reprecipitation with Cl$_2$CH$_2$ and n-hexane, a compound DAT (white powder) was obtained with a yield of 38%.

The synthesis pathway was as follows:

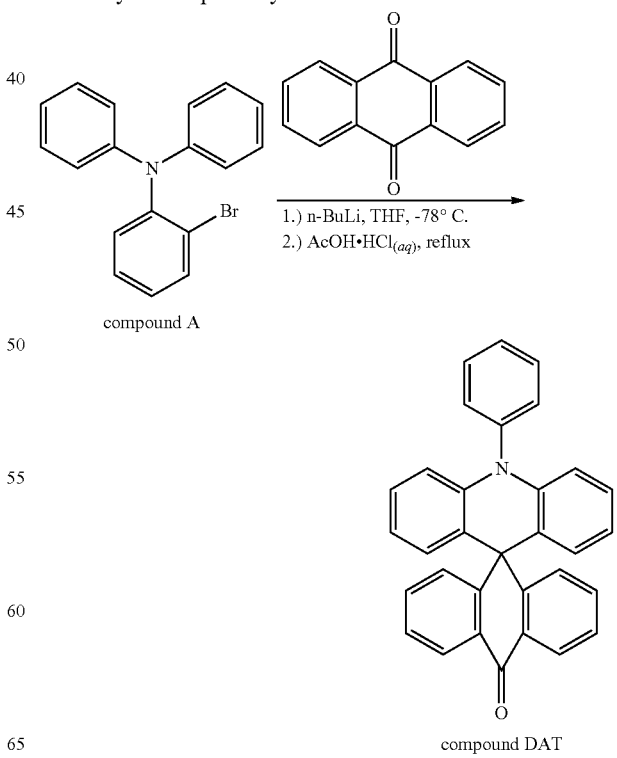

compound DAT

Next, the TG, HOMO and LUMO energy gap, melting point, phosphorescent wavelength (measured at −78° C.), and ¹Eg of compound DAT were measured and are shown in Table 2.

EXAMPLE 13

Preparation of Compound DTAT

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr, anthraquinone-2-t-butane (10.0 mmole, 2.66 g) was added into the bottle. After reacting at room temperature for 2 hrs, AcOH (30 ml) was added into the bottle and refluxed for 3 hrs. Next, the results was extracted by Cl₂CH₂ and dried by MgSO₄, and compound DTAT (white powder) was obtained via concentration.

The synthesis pathway was as follows:

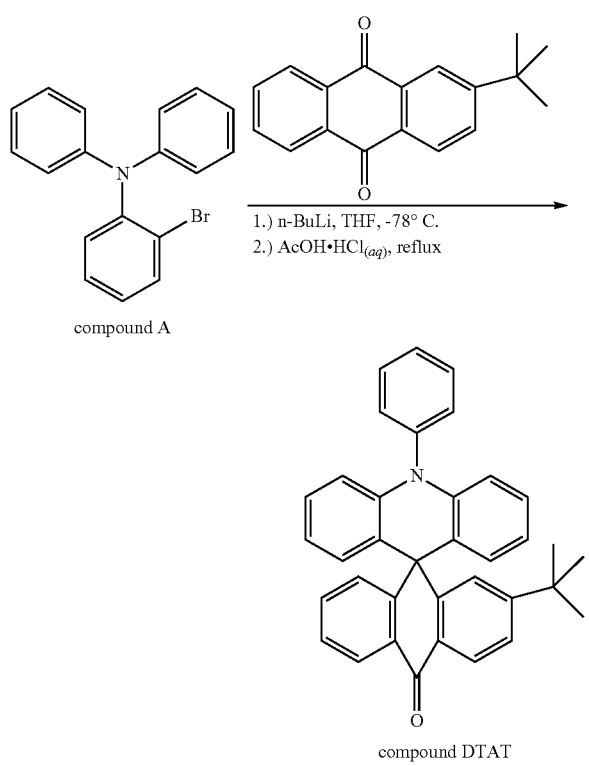

compound DTAT

EXAMPLE 15

Preparation of Compound DEAT

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr,

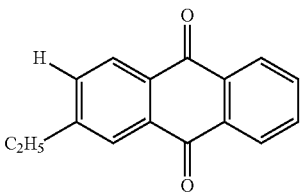 [SMILES: CCc1ccc2c(c1)C(=O)c1ccccc1C2=O]

(10.0 mmole) was added into the bottle. After reacting at room temperature for 2 hrs, AcOH (30 ml) was added into the bottle and refluxed for 3 hrs. Next, the results was extracted by Cl₂CH₂ and dried by MgSO₄, and compound DEAT (white powder) was obtained via concentration.

The synthesis pathway was as follows:

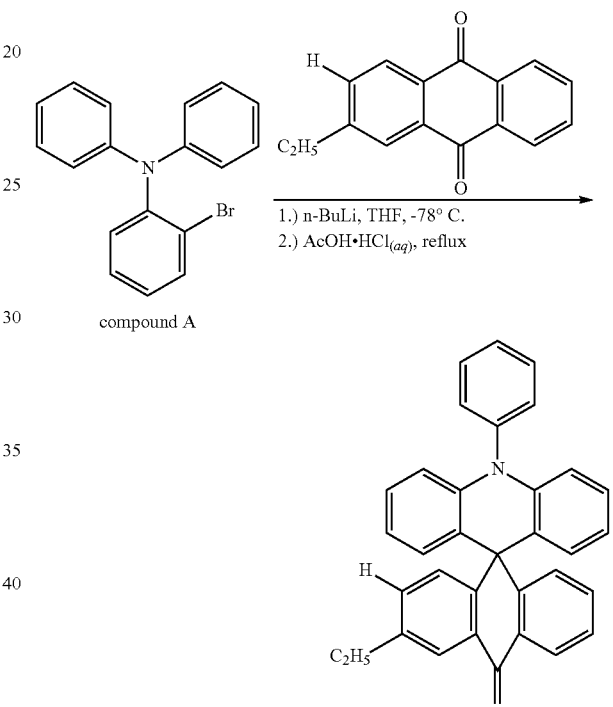

EXAMPLE 16

Preparation of Compound DMAT

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr,

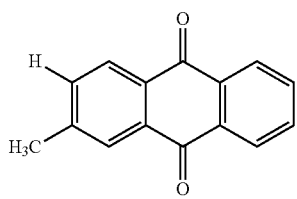 [SMILES: Cc1ccc2c(c1)C(=O)c1ccccc1C2=O]

(10.0 mmole) was added into the bottle. After reacting at room temperature for 2 hrs, AcOH (30 ml) was added into the bottle and refluxed for 3 hrs. Next, the results was extracted by Cl$_2$CH$_2$ and dried by MgSO$_4$, and compound DMAT (white powder) was obtained via concentration.

The synthesis pathway was as follows:

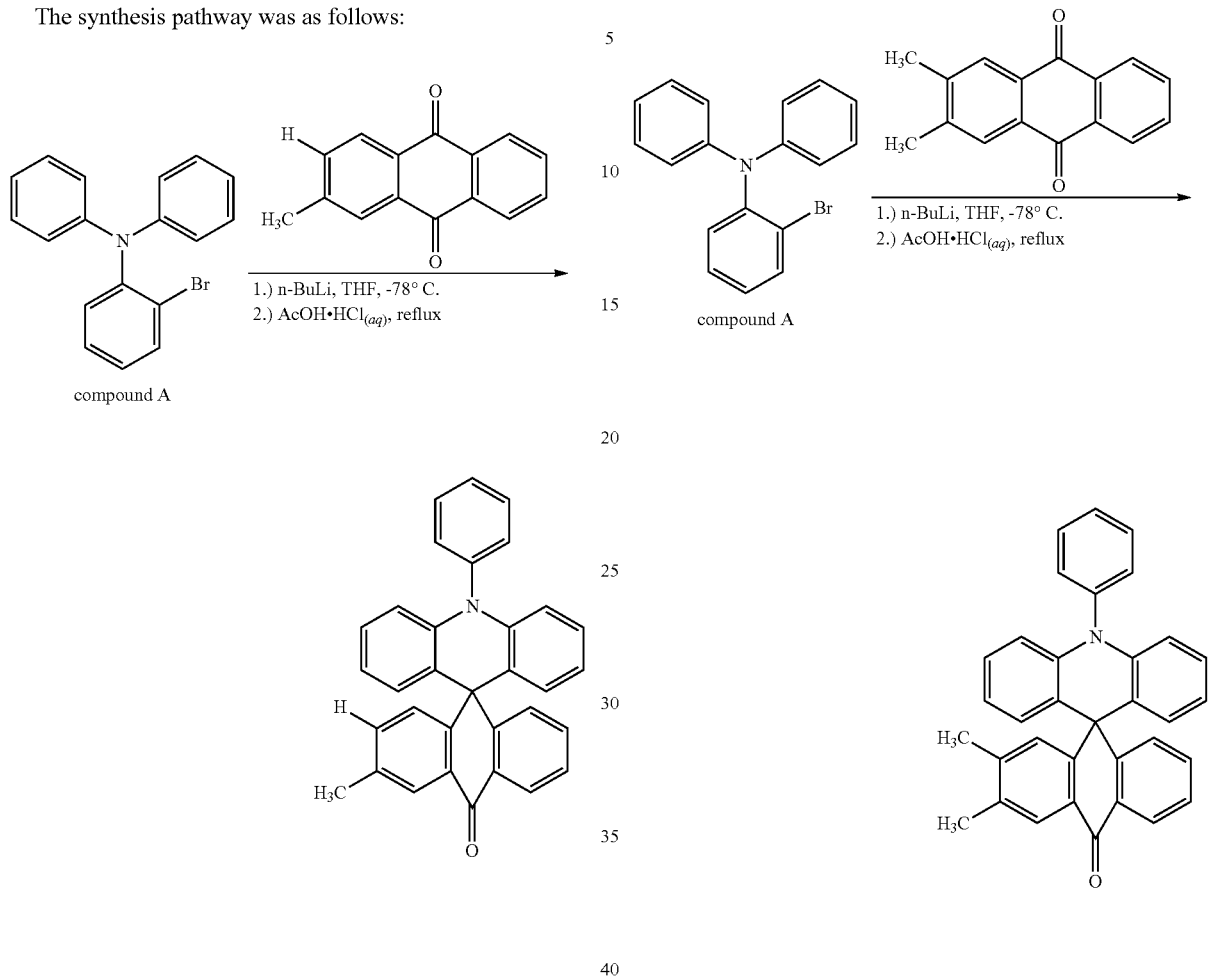

compound A

EXAMPLE 17

Preparation of Compound DDMAT

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr,

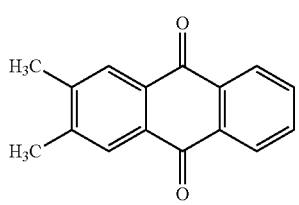

(10.0 mmole) was added into the bottle. After reacting at room temperature for 2 hrs, AcOH (30 ml) was added into the bottle and refluxed for 3 hrs. Next, the results was extracted by Cl$_2$CH$_2$ and dried by MgSO$_4$, and compound DDMAT (white powder) was obtained via concentration.

The synthesis pathway was as follows:

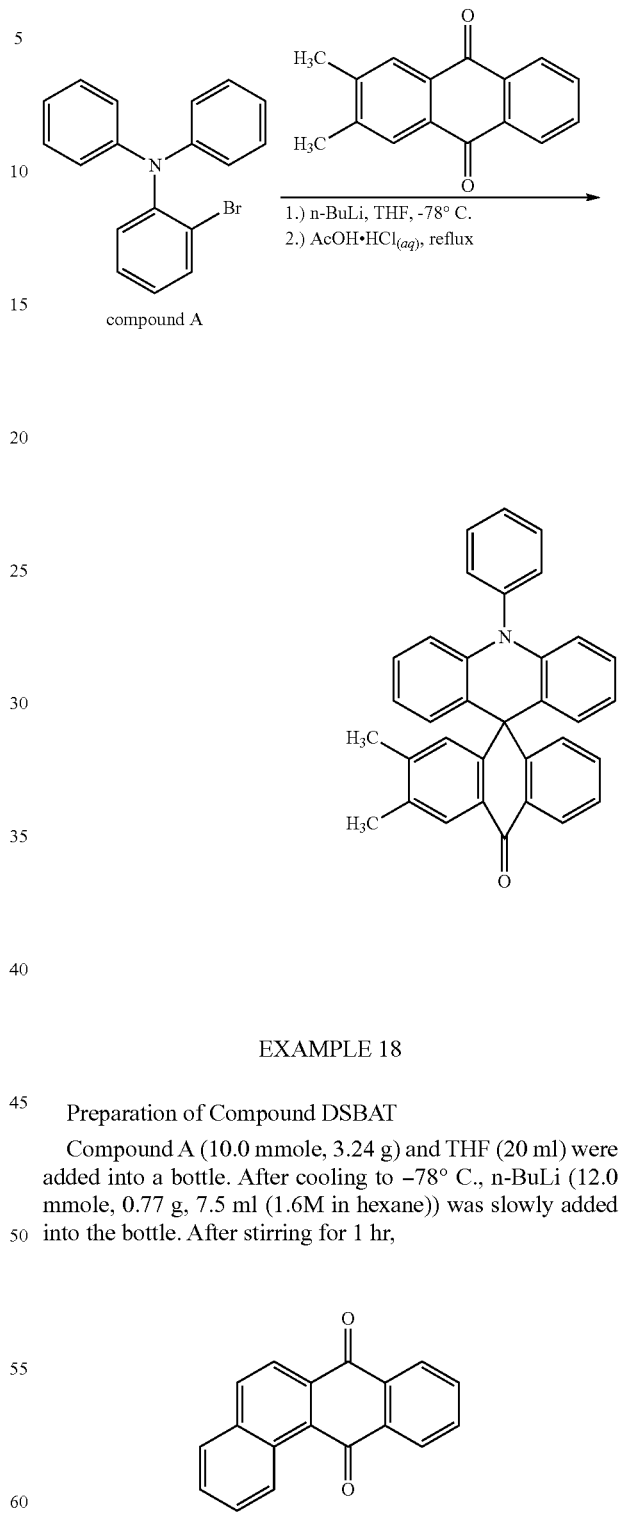

EXAMPLE 18

Preparation of Compound DSBAT

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr,

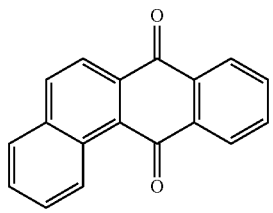 [SMILES: O=C1c2ccccc2C(=O)c2c1ccc1ccccc21]

(10.0 mmole) was added into the bottle. After reacting at room temperature for 2 hrs, AcOH (30 ml) was added into the bottle and refluxed for 3 hrs. Next, the results was extracted by Cl$_2$CH$_2$ and dried by MgSO$_4$, and compound DSBAT (white powder) was obtained via concentration.

The synthesis pathway was as follows:

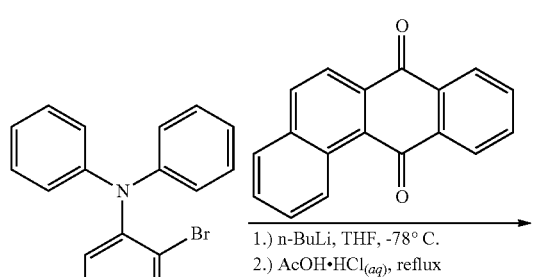

compound A

EXAMPLE 19

Preparation of Compound DBAT

Compound A (10.0 mmole, 3.24 g) and THF (20 ml) were added into a bottle. After cooling to −78° C., n-BuLi (12.0 mmole, 0.77 g, 7.5 ml (1.6M in hexane)) was slowly added into the bottle. After stirring for 1 hr,

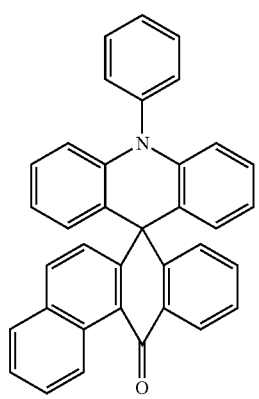

(10.0 mmole) was added into the bottle. After reacting at room temperature for 2 hrs, AcOH (30 ml) was added into the bottle and refluxed for 3 hrs. Next, the results was extracted by $Cl_2CH_2$ and dried by $MgSO_4$, and compound DBAT (white powder) was obtained via concentration.

The synthesis pathway was as follows:

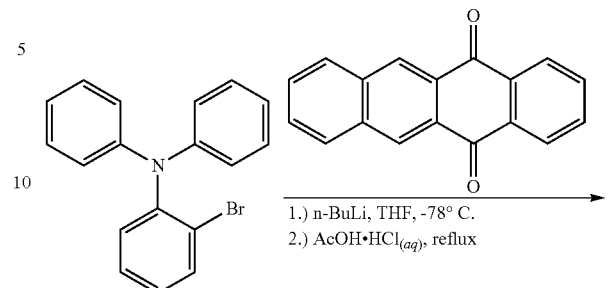

compound A

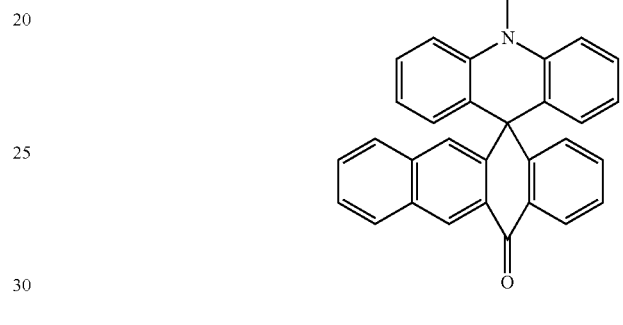

Next, the TG, HOMO and LUMO energy gap, melting point, phosphorescent wavelength (measured at −78° C.), and $^1$Eg of compound DTAT were measured and are shown in Table 2.

TABLE 2

| Compound | HOMO (eV) | LUMO (eV) | Tg (° C.) | Tm (° C.) | wavelength(nm) | tEg (eV) |
|---|---|---|---|---|---|---|
| TB | 5.42 | 1.74 | — | 254 | 403 | 3.08 |
| TF | 5.29 | 1.71 | 79 | 282 | 410 | 3.02 |
| TBM | 5.41 | 1.64 | — | 232 | 403 | 3.08 |
| DAT | 5.51 | 1.92 | — | 329 | 468 | 2.94 |
| DTAT | 5.45 | 1.86 | 117 | 293 | 420 | 2.95 |
| TBP | 5.52 | 2.00 | 115 | 309 | 409 | 3.03 |

Organic Electroluminescence Device

FIG. 1 shows an embodiment of an organic electroluminescent device 10. The electroluminescent device 100 includes a substrate 12, a bottom electrode 14, an electroluminescent element 16, and a top electrode 18, as shown in FIG. 1. The organic electroluminescent device can be top-emission, bottom-emission, or dual-emission devices.

The substrate 12 can be a glass plastic, or semiconductor substrate. Suitable material for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Further, al least one of the bottom and top electrodes 14 and 18 is transparent.

The electroluminescent element 16 at least includes an emission layer, and can further include a hole injection layer, a hole transport layer, an electron transport layer, and an electron injection layer. In embodiment of the invention, at least one layer of the electroluminescent element 16 includes the aforementioned organic compound.

According to an embodiment of the invention, the organic electroluminescent device can be a phosphorescent organic electroluminescent device, and the phosphorescent organic electroluminescent device can include an emission layer including a host material and a phosphorescent dopant, wherein the host material includes the aforementioned organic compounds.

In order to clearly disclose the organic electroluminescent devices of the invention, the following examples (using DAT and TBP as host materials and blue or green phosphorescent dopant) and comparative examples are intended to illustrate the invention more fully without limiting their scope, since numerous modifications and variations will be apparent to those skilled in this art.

EXAMPLE 20

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA (4,4',4''-tri(N-carbazolyl) triphenylamine), with a thickness of 30 nm), DAT doped with Firpic (Iridium-bis(4,6difluorophenyl-pyridinato-N,C2)-picolinate) (the ratio between DAT and Firpic was 100:6, with a thickness of 30 nm), TPBI (1,3,5-tris(phenyl-2-benzimidazolyl)-benzene), with a thickness of 30 nm), LiF (with a thickness of 1 nm), and Al (with a thickness of 100 nm) were subsequently formed on the ITO film at $10^{-5}$ Pa, obtaining the electroluminescent device (1). The materials and layers formed therefrom are described in the following.

The emissive structure of the electroluminescent device (1) can be represented as follows: ITO/TCTA/Firpic:DAT 6%/TPBI/LiF/Al.

The optical property of the electroluminescent device (1), as described in Example 15, was measured by a PR650 (purchased from Photo Research Inc.) and a Minolta TS110. The result is shown in Table 3.

EXAMPLE 21

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA ((4,4',4''-tri(N-carbazolyl) triphenylamine), with a thickness of 30 nm), DAT doped with Firpic (Iridium-bis(4,6difluorophenyl-pyridinato-N,C2)-picolinate) (the ratio between DAT and Firpic was 100:6, with a thickness of 30 nm), BCP (2,9-dimethyl-4,7diphenyl-1,10-phenanthroline), with a thickness of 30 nm), $Alq_3$ (tris(8-hydroxyquinoline) aluminum), with a thickness of 30 nm), LiF (with a thickness of 1 nm), and Al (with a thickness of 100 nm) were subsequently formed on the ITO film at $10^{-5}$ Pa, obtaining the electroluminescent device (2).

The emissive structure of the electroluminescent device (2) can be represented as follows: ITO/TCTA/Firpic:DAT 6%/BCP/$Alq_3$/LiF/Al.

The optical property of the electroluminescent device (2), as described in Example 16, was measured by a PR650 (purchased from Photo Research Inc.) and a Minolta TS110. The result is shown in Table 3.

EXAMPLE 22

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA ((4,4',4''-tri(N-carbazolyl) triphenylamine), with a thickness of 30 nm), DAT doped with Firpic (Iridium-bis(4,6difluorophenyl-pyridinato-N,C2)-picolinate) (the ratio between DAT and Firpic was 100:6, with a thickness of 30 nm), BPhen (4,7-diphenyl-1,10-phenanthroline), with a thickness of 30 nm), LiF (with a thickness of 1 nm), and Al (with a thickness of 100 nm) were subsequently formed on the ITO film at $10^{-5}$ Pa, obtaining the electroluminescent device (3).

The emissive structure of the electroluminescent device (3) can be represented as follows: ITO/TCTA/Firpic:DAT 6%/BPhen/LiF/Al.

The optical property of the electroluminescent device (3), as described in Example 17, was measured by a PR650 (purchased from Photo Research Inc.) and a Minolta TS110. The result is shown in Table 3.

EXAMPLE 23

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA (4,4',4''-tri(N-carbazolyl) triphenylamine), with a thickness of 30 nm), DAT doped with Firpic (Iridium-bis(4,6difluorophenyl-pyridinato-N,C2)-picolinate) (the ratio between DAT and Firpic was 100:9, with a thickness of 30 nm), TPBI (1,3,5-tris(phenyl-2-benzimidazolyl)-benzene, with a thickness of 30 nm), LiF (with a thickness of 1 nm), and Al (with a thickness of 100 nm) were subsequently formed on the ITO film at $10^{-5}$ Pa, obtaining the electroluminescent device (4).

The emissive structure of the electroluminescent device (4) can be represented as follows: ITO/TCTA/Firpic:DAT 9%/TPBI/LiF/Al.

The optical property of the electroluminescent device (4), as described in Example 18, was measured by a PR650 (purchased from Photo Research Inc.) and a Minolta TS 110. The result is shown in Table 3.

COMPARATIVE EXAMPLE 1

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA (4,4',4''-tri(N-carbazolyl) triphenylamine), with a thickness of 30 nm), CBP doped with Firpic (Iridium-bis(4,6difluorophenyl-pyridinato-N,C2)-picolinate) (the ratio between CBP and Firpic was 100:6, with a thickness of 30 nm), TPBI (1,3,5-tris(phenyl-2-benzimidazolyl)-benzene), with a thickness of 30 nm), LiF (with a thickness of 1 nm), and Al (with a thickness of 100 nm) were subsequently formed on the ITO film at $10^{-5}$ Pa, obtaining the electroluminescent device (5).

The emissive structure of the electroluminescent device (5) can be represented as follows: ITO/TCTA/Firpic:CBP 6%/TPBI/LiF/Al.

The optical property of the electroluminescent device (5), as described in the Comparative Example 1, was measured by a PR650 (purchased from Photo Research Inc.) and a Minolta TS 110. The result is shown in Table 3.

TABLE 3

|  | brightness (cd/m2) | power efficiency (lm/W) | current efficiency (cd/A) | CIE |
|---|---|---|---|---|
| electroluminescent device (1) | 4644 (under 11 V) | 7.19 (under 4 V) | 9.16 (under 4 V) | (0.12, 0.29) |
| electroluminescent device (2) | 1733 (under 11 V) | 5.72 (under 6.5 V) | 2.57 (under 6.5 V) | (0.11, 0.29) |
| electroluminescent device (3) | 6668 (under 10.5 V) | 5.86 (under 4.5 V) | 8.39 (under 4.5 V) | (0.12, 0.30) |
| electroluminescent device (4) | 2200 (under 11 V) | 10.2 (under 5.5 V) | 5.9 (under 5.5 V) | (0.12, 0.28) |
| electroluminescent device (5) | 1532 (under 13 V) | 3.27 (under 6.5 V) | 1.6 (under 6.5 V) | (0.26, 0.45) |

EXAMPLE 24

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA ((4,4',4"-tri(N-carbazolyl) triphenylamine), with a thickness of 30 nm), DAT doped with Ir(ppy)$_3$ (Tris(2-phenylpyridine)iridium) (the ratio between DAT and Ir(ppy)$_3$ was 100:6, with a thickness of 30 nm), BCP ((2,9-dimethyl-4,7diphenyl-1,10-phenanthroline), with a thickness of 30 nm), Alq$_3$ ((tris(8-hydroxyquinoline) aluminum), with a thickness of 30 nm), LiF (with a thickness of 1 nm), and Al (with a thickness of 100 nm) were subsequently formed on the ITO film at $10^{-5}$ Pa, obtaining the electroluminescent device (6). The materials and layers formed therefrom are described in the following.

The emissive structure of the electroluminescent device (6) can be represented as follows: ITO/TCTA/Ir(ppy)$_3$:DAT 6%/BCP/Alq$_3$/LiF/Al.

The optical property of the electroluminescent device (6), as described in Example 19, was measured by a PR650 (purchased from Photo Research Inc.) and a Minolta TS 110. The result is shown in Table 4.

EXAMPLE 25

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA ((4,4',4"-tri(N-carbazolyl) triphenylamine), with a thickness of 30 nm), DAT doped with Ir(ppy)$_3$ (Tris(2-phenylpyridine)iridium) (the ratio between DAT and Ir(ppy)$_3$ was 100:6, with a thickness of 30 nm), TPBI((1,3,5-tris(phenyl-2-benzimidazolyl)-benzene), with a thickness of 30 nm), LiF (with a thickness of 1 nm), and Al (with a thickness of 100 nm) were subsequently formed on the ITO film at $10^{-5}$ Pa, obtaining the electroluminescent device (7).

The emissive structure of the electroluminescent device (7) can be represented as follows: ITO/TCTA/Ir(ppy)$_3$:DAT 6%/TPBI/LiF/Al.

The optical property of the electroluminescent device (7), as described in Example 20, was measured by a PR650 (purchased from Photo Research Inc.) and a Minolta TS110. The result is shown in Table 3.

EXAMPLE 26

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA ((4,4',4"-tri(N-carbazolyl) triphenylamine), with a thickness of 30 nm), DAT doped with Ir(ppy)$_3$ (Tris(2-phenylpyridine)iridium) (the ratio between DAT and Ir(ppy)$_3$ was 100:6, with a thickness of 30 nm), BCP ((2,9-dimethyl-4,7diphenyl-1,10-phenanthroline), with a thickness of 30 nm), Alq$_3$ ((tris(8-hydroxyquinoline) aluminum), with a thickness of 30 nm), LiF (with a thickness of 1 nm), and Al (with a thickness of 100 nm) were subsequently formed on the ITO film at $10^{-5}$ Pa, obtaining the electroluminescent device (8).

The emissive structure of the electroluminescent device (8) can be represented as follows: ITO/TCTA/Ir(ppy)$_3$:DAT 9%/BCP/Alq$_3$/LiF/Al.

The optical property of the electroluminescent device (8), as described in Example 21, was measured by a PR650 (purchased from Photo Research Inc.) and a Minolta TS110. The result is shown in Table 4.

COMPARATIVE EXAMPLE 2

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA ((4,4',4"-tri(N-carbazolyl) triphenylamine), with a thickness of 30 nm), CBP doped with Ir(ppy)$_3$ (Tris(2-phenylpyridine)iridium) (the ratio between CBP and Ir(ppy)$_3$ was 100:6, with a thickness of 30 nm), BCP ((2,9-dimethyl-4,7diphenyl-1,10-phenanthroline), with a thickness of 30 nm), Alq$_3$ ((tris(8-hydroxyquinoline) aluminum), with a thickness of 30 nm), LiF (with a thickness of 1 nm), and Al (with a thickness of 100 nm) were subsequently formed on the ITO film at $10^{-5}$ Pa, obtaining the electroluminescent device (9).

The emissive structure of the electroluminescent device (9) can be represented as follows: ITO/CTA/Ir(ppy)$_3$:CBP 6%/BCP/Alq$_3$/LiF/Al.

The optical property of the electroluminescent device (9), as described in the Comparative Example 2, was measured by a PR650 (purchased from Photo Research Inc.) and a Minolta TS 110. The result is shown in Table 4.

TABLE 4

|  | brightness (cd/m2) | power efficiency (lm/W) | current efficiency (cd/A) | CIE |
|---|---|---|---|---|
| electroluminescent device (6) | 4644 (under 11 V) | 7.19 (under 4 V) | 9.16 (under 4 V) | (0.33, 0.61) |
| electroluminescent device (7) | 1733 (under 11 V) | 5.72 (under 6.5 V) | 2.57 (under 6.5 V) | (0.37, 0.58) |
| electroluminescent device (8) | 6668 (under 10.5 V) | 5.86 (under 4.5 V) | 8.39 (under 4.5 V) | (0.27, 0.62) |
| electroluminescent device (9) | 2100 (under 11 V) | 10.2 (under 5.5 V) | 5.9 (under 5.5 V) | (0.33, 0.60) |

As shown in Table 4, on the premise of the same green dopant, the organic compound DAT of the invention has superior efficiency and brightness in compliance with conventional organic host material CBP.

EXAMPLE 27

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, TCTA ((4,4',4"-tri(N-carbazolyl)triphenylamine), with a thickness of 30 nm), TBP doped with Firpic (Iridium-bis(4,6difluorophenyl-pyridinato-N,C2)-picolinate) (the ratio between TBP and Firpic was 100:6, with a thickness of 30 nm), TPBI (1,3,5-tris(phenyl-2-benzimidazolyl)-benzene), with a thickness of 30 nm), LiF (with a thickness of 1 nm), and Al (with a thickness of 100 nm) were subsequently formed on the ITO film at $10^{-5}$ Pa, obtaining the electroluminescent device (10).

The emissive structure of the electroluminescent device (10) can be represented as follows: ITO/TCTA/Firpic:TBP 6%/TPBI/LiF/Al The optical property of the electroluminescent device (10), as described in Example 22, was measured by a PR650 (purchased from Photo Research Inc.) and a Minolta TS110. The result is shown in Table 5.

EXAMPLE 28

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, 2-TNATA ((4,4',4"-Tris-(N-(naphthylen-2-yl)-N-phenylamine)triphenylamine), with a thickness of 30 nm), DAT doped with Firpic (Iridium-bis(4,6difluorophenyl-pyridinato-N,C2)-picolinate) (the ratio between DAT and Firpic was 100:6, with a thickness of 30 nm), TPBI (1,3,5-tris(phenyl-2-benzimidazolyl)-benzene), with a thickness of 30 nm), LiF (with a thickness of 1 nm), and Al (with a thickness of 100 nm) were subsequently formed on the ITO film at $10^{-5}$ Pa, obtaining the electroluminescent device (11).

The emissive structure of the electroluminescent device (11) can be represented as follows: ITO/2-TNATA/Firpic:TBP 6%/TPBI/LiF/Al The optical property of the electroluminescent device (11), as described in Example 23, was measured by a PR650 (purchased from Photo Research Inc.) and a Minolta TS110. The result is shown in Table 5.

EXAMPLE 29

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, 2-TNATA ((4,4',4"-Tris-(N-(naphthylen-2-yl)-N-phenylamine)triphenylamine), with a thickness of 30 nm), DAT doped with Firpic (Iridium-bis(4,6difluorophenyl-pyridinato-N,C2)-picolinate) (the ratio between DAT and Firpic was 100:6, with a thickness of 30 nm), TAZ(3-phenyl-4-(1-naphthyl)-5-phenyl1,2,4-triazole), with a thickness of 15 nm), TPBI (1,3,5-tris(phenyl-2-benzimidazolyl)-benzene), with a thickness of 20 nm), LiF (with a thickness of 1 nm), and Al (with a thickness of 100 nm) were subsequently formed on the ITO film at $10^{-5}$ Pa, obtaining the electroluminescent device (12).

The emissive structure of the electroluminescent device (12) can be represented as follows: ITO/2-TNATA/Firpic:TBP 6%/TAZ/TPBI/LiF/Al The optical property of the electroluminescent device (12), as described in Example 24, was measured by a PR650 (purchased from Photo Research Inc.) and a Minolta TS110. The result is shown in Table 5.

EXAMPLE 30

A glass substrate with an indium tin oxide (ITO) film of 120 nm was provided and then washed with a cleaning agent, acetone, and isopropanol with ultrasonic agitation. After drying with nitrogen flow, the ITO film was subjected to a UV/ozone treatment. Next, 2-TNATA ((4,4',4"-Tris-(N-(naphthylen-2-yl)-N-phenylamine)triphenylamine), with a thickness of 30 nm), TBP (with a thickness of 3 nm), TBP doped with Firpic (Iridium-bis(4,6difluorophenyl-pyridinato-N,C2)-picolinate) (the ratio between TBP and Firpic was 100:6, with a thickness of 30 nm), TAZ(3-phenyl-4-(1-naphthyl)-5-phenyl 1,2,4-triazole), with a thickness of 15 nm), TPBI (1,3,5-tris(phenyl-2-benzimidazolyl)-benzene), with a thickness of 20 nm), LiF (with a thickness of 1 nm), and Al (with a thickness of 100 nm) were subsequently formed on the ITO film at $10^{-5}$ Pa, obtaining the electroluminescent device (13).

The emissive structure of the electroluminescent device (13) can be represented as follows: ITO/2-TNATA/TBP/Firpic:TBP6%/TAZ/TPBI/LiF/Al The optical property of the electroluminescent device (13), as described in Example 25, was measured by a PR650 (purchased from Photo Research Inc.) and a Minolta TS 110. The result is shown in Table 5.

TABLE 5

|  | brightness (cd/m2) | power efficiency (lm/W) | current efficiency (cd/A) | CIE |
| --- | --- | --- | --- | --- |
| electroluminescent device (11) | 4644 (under 11 V) | 7.19 (under 4 V) | 9.16 (under 4 V) | (0.33, 0.61) |
| electroluminescent device (12) | 1733 (under 11 V) | 5.72 (under 6.5 V) | 2.57 (under 6.5 V) | (0.37, 0.58) |
| electroluminescent device (13) | 6668 (under 10.5 V) | 5.86 (under 4.5 V) | 8.39 (under 4.5 V) | (0.27, 0.62) |
| electroluminescent device (14) | 2100 (under 11 V) | 10.2 (under 5.5 V) | 5.9 (under 5.5 V) | (0.33, 0.60) |

Accordingly, the organic compounds of Formula (I) of the invention have high triplet energy ($^1Eg$) gap and are apt to transmit energy to a guest emitter. Therefore, the organic compounds of Formula (I) of the invention are suitable for serving as host material of the blue or green phosphorescent organic electroluminescent devices, thereby increasing efficiency thereof.

While the invention has been described by way of example and in terms of embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic compound having a Formula (I), of:

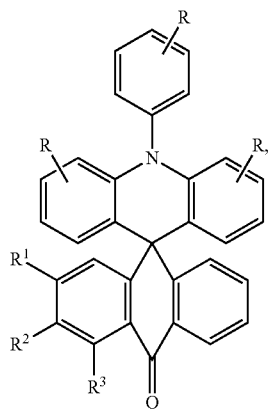

(I)

wherein R are each independently a hydrogen, or a $C_{1-8}$ alkyl group, and wherein, one of following three conditions is satisfied:

(I) $R^1$ and $R^2$ are each independently a hydrogen, or a $C_{1-8}$ alkyl group, $R^3$ is a hydrogen, and $R^1$ and $R^2$ are not hydrogen group simultaneously;

(II) $R^1$ and $R^2$ link together with the carbon atoms to which $R^1$ and $R^2$ are attached to form a phenyl group, and $R^3$ is a hydrogen; and (III) $R^2$ and $R^3$ link together with the carbon atoms to which $R^2$ and $R^3$ are attached to form a phenyl group, and $R^1$ is a hydrogen, or a $C_{1-8}$ alkyl group.

2. The organic compound as claimed in claim 1, wherein $R^1$, and $R^2$ are each independently a methyl group, ethyl group, propyl group, isopropyl group, butyl group, or tert-butyl group.

3. The organic compound as claimed in claim 1, wherein the organic

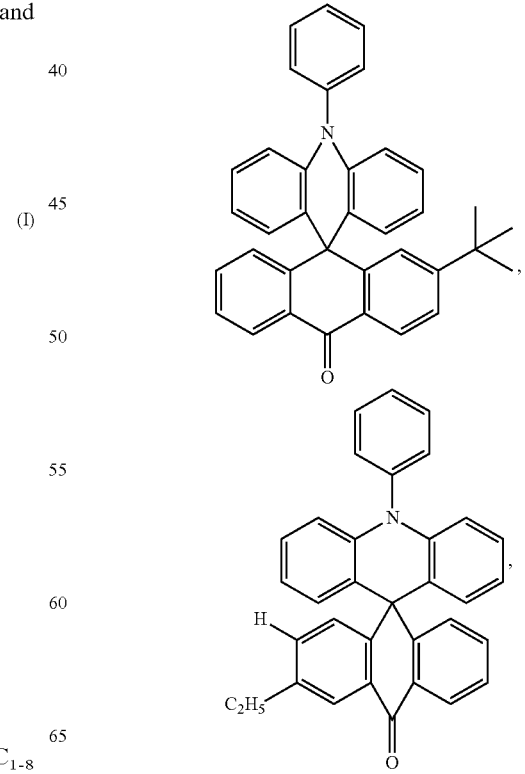

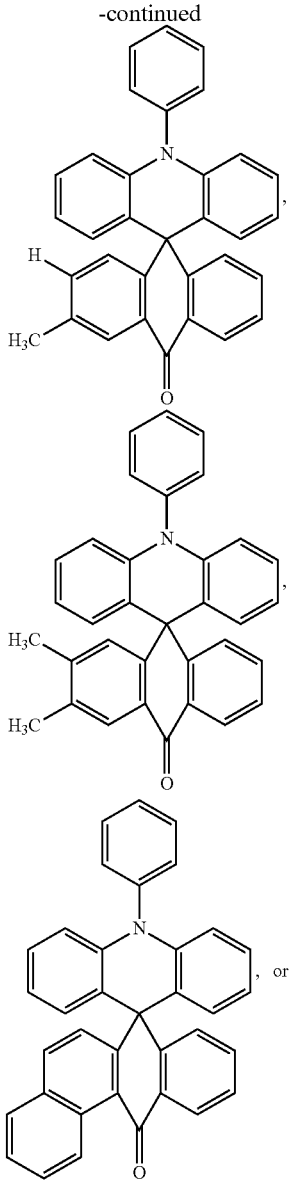, 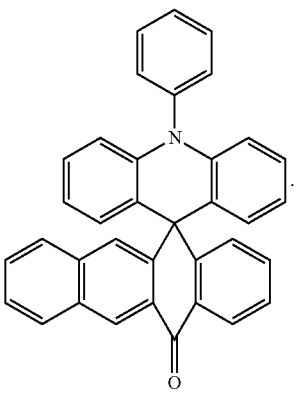

compound is

4. An organic electroluminescence device, comprising:

a pair of electrodes; and an electroluminescent element disposed between the pair of electrodes, wherein the electroluminescent element comprises the organic compound as claimed in claim 1.

5. An organic electroluminescence device, comprising:

a pair of electrodes; and an electroluminescent element disposed between the pair of electrodes, wherein the electroluminescent element comprises an emission layer comprising a host material and a phosphorescent dopant, and the host material comprises the organic compound as claimed in claim 1.

6. The organic electroluminescence device as claimed in claim 5, wherein the emission layer emits blue or green light under a bias voltage.

* * * * *